(12) United States Patent
Tang et al.

(10) Patent No.: US 12,325,732 B2
(45) Date of Patent: Jun. 10, 2025

(54) PRO-INSULIN ASPART STRUCTURE AND METHOD FOR PREPARING INSULIN ASPART

(71) Applicant: AMPHASTAR NANJING PHARMACEUTICALS INC, Jiangsu (CN)

(72) Inventors: Chuangen Tang, Jiangsu (CN); Shangshu Pan, Jiangsu (CN); Xiaorui Liu, Jiangsu (CN); Cheng Li, Jiangsu (CN); Huaiyan Cui, Jiangsu (CN); Song Chen, Jiangsu (CN); Haoning Zhang, Jiangsu (CN); Jeffrey Ding, Jiangsu (CN)

(73) Assignee: AMPHASTAR NANJING PHARMACEUTICALS INC, Jiangsu (CN)

( * ) Notice: Subject to any disclaimer, the term of this patent is extended or adjusted under 35 U.S.C. 154(b) by 1043 days.

(21) Appl. No.: 17/275,821

(22) PCT Filed: Sep. 12, 2018

(86) PCT No.: PCT/CN2018/105314
§ 371 (c)(1),
(2) Date: Mar. 12, 2021

(87) PCT Pub. No.: WO2020/051812
PCT Pub. Date: Mar. 19, 2020

(65) Prior Publication Data
US 2021/0332100 A1   Oct. 28, 2021

(51) Int. Cl.
*C07K 14/62*   (2006.01)

(52) U.S. Cl.
CPC .................... *C07K 14/62* (2013.01)

(58) Field of Classification Search
CPC .. C07K 14/62; A61K 38/00; C12Y 115/01001
See application file for complete search history.

(56) References Cited

U.S. PATENT DOCUMENTS

| | | | |
|---|---|---|---|
| 5,547,930 A | 8/1996 | Balschmidt | |
| 5,618,913 A | 4/1997 | Brange et al. | |
| 5,834,422 A | 11/1998 | Balschmidt | |
| 6,001,604 A | 12/1999 | Hartman et al. | |
| 6,777,207 B2 * | 8/2004 | Kjeldsen et al. | C07K 14/62 |
| 6,875,589 B1 | 4/2005 | Dorschug et al. | |
| 9,187,520 B2 * | 11/2015 | Wang et al. | C07K 14/62 |
| 2014/0221606 A1 * | 8/2014 | Zimmerman et al. | C07K 14/62 |

FOREIGN PATENT DOCUMENTS

| | | | |
|---|---|---|---|
| CN | 86106574 A | 8/1988 | |
| CN | 1177928 A | 4/1998 | |
| CN | 1873006 A | 12/2006 | |
| CN | 101519446 A | 9/2009 | |
| EP | 0055945 A2 | 7/1982 | |
| EP | 0163529 A1 | 12/1985 | |
| WO | WO 96/20724 * | 7/1996 | |
| WO | WO-9620724 A1 * | 7/1996 | ............... A61P 3/10 |
| WO | WO 2017/041001 A2 * | 3/2017 | |

OTHER PUBLICATIONS

Chang et al. Human insulin production from a novel mini-proinsulin which has high receptor-binding activity, 1998, Biochemical Journal, 329: 631-635 (Year: 1998).*
Labconco,A guide to freeze drying for the laboratory, 2004 <http://www.thermofishersci.in/lit/Labconco%20-%20A%20laboratory%20guide%20to%20freeze%20drying.pdf> Last accessed Apr. 24, 2024. (Year: 2004).*
Pink , Drying Technology, 2024, <https://www.pink.de/en/products/vacuum-drying-systems.html> last accessed Apr. 24, 2024. (Year: 2024).*
Novagen, pET Manual System, 1999, <https://research.fredhutch.org/content/dam/stripe/hahn/methods/biochem/pet.pdf> last accessed Apr. 24, 2024 (Year: 1999).*
Biocompare, Peptide synthesis: What level of purity do you need? 2012, <https://www.biocompare.com/Editorial-Articles/117894-Peptide-Synthesis/> last accessed Apr. 24, 2024 (Year: 2012).*
Fujinari et al.,Peptide content determination of crude synthetic peptides by reversed-phase liquid chromatography and nitrogen-specific detection with a chemiluminescent nitrogen detector, 1996, Journal of Chromatography A, 743: 85-89 (Year: 1996).*
Farkas et al.,Cost-Effective Flow Peptide Synthesis: Metamorphosis of HPLC, 2021, Organic Process Research and Development, 25: 182-191) (Year: 2021).*
Conlon, Purification of naturally occurring peptides by reversed-phase HPLC, 2007, Nature Protocols, 2: 191-197) (Year: 2007).*
Setter et al., Insulin Aspart: A New Rapid-Acting Insulin Analog, 2000, The Annals of Pharmacotherapy, 34, 1423-1431 (Year: 2000).*
Ahmed et al., Synthesis, cloning and expression of a novel pre-miniproinsulin analogue gene in *Escherichia coli*, 2015, Journal of Advanced Research, 6: 663-671 (Year: 2015).*

(Continued)

*Primary Examiner* — Lianko G Garyu
*Assistant Examiner* — Claudia Espinosa
(74) *Attorney, Agent, or Firm* — HAUPTMAN HAM, LLP (57) ABSTRACT

Provided are a novel pro-insulin aspart structure design and a method for preparing the pro-insulin aspart. The method comprises designing the pro-insulin aspart sequence, constructing a recombinant insulin aspart engineered bacteria, inducing expression of an insulin fusion protein as an inclusion body in the engineered bacteria, and extracting the insulin fusion protein from the engineered bacteria by means of denaturing, renaturing enzymatic digestion, and separation purification operations. By modifying the recombinant leading peptide and C-peptide sequences, the method avoids the need to include a cyanogen bromide cleavage step. In some embodiments, the C-peptide is replaced by a single amino acid which tends to reduce quality loss associated with enzymatic digestion.

9 Claims, 1 Drawing Sheet
Specification includes a Sequence Listing.

(56) References Cited

OTHER PUBLICATIONS

Extended European Search Report issued in corresponding European Application No. 18933038.4; mailed Oct. 5, 2021; 7 pgs.
Chen, Y. et al., "Improving the refolding efficiency for proinsulin aspart inclusion body with optimized buffer compositions", Protein Expression and Purification, vol. 122, Jan. 28, 2016, XP029520907; 7 pgs.

* cited by examiner

PRO-INSULIN ASPART STRUCTURE AND METHOD FOR PREPARING INSULIN ASPART

RELATED APPLICATIONS

The present application is a National Phase of International Application Number PCT/CN2018/105314 filed Sep. 12, 2018.

INCORPORATION BY REFERENCE

The sequence listing provided in the file entitled SQL_Amended_2021-07-14.txt, which is an ASCII text file that was created on Jul. 14, 2021, and which comprises 12,278 bytes, is hereby incorporated by reference in its entirety.

TECHNICAL FIELD

The invention relates to the technical field of polypeptide preparation methods, in particular to a new short-proinsulin aspart design and methods of producing insulin aspart therefrom.

BACKGROUND

Insulin is a hormone that regulates glucose metabolism in animals. This hormone is made up of two polypeptide chains, an A-chain of 21 amino acids, and a B-chain of 30 amino acids, a total of 51 amino acids. Wherein four cysteines $A_7$ (Cys)-$B_7$ (Cys), $A_{20}$ (Cys)-$B_{19}$ (Cys) form two disulfide bonds, the two disulfide bonds connect A, B two chains. In the A-chain, $A_6$ (Cys) and $A_{11}$ (Cys) form an intrachain disulfide bond. Diabetes mellitus is characterized by elevated blood glucose levels as a result of insulin deficiency and/or increased hepatic glucose production. Insulin is a medicine for patients with diabetes.

The overall goal for the development of insulin analog is to mimic physiological insulin secretion, thereby improve glycemic control of patients with type 1 and type 2 diabetes (Berger M, *A comment. Diabetes Res Clin Pract.* 6: S25-S31, 1989 and Nosek L. et al, *Diabetes, Obesity and Metabolism,* 15: 77-83, 2013.).

Recent insulin analogs (analogs of naturally occurring insulin) include additional or substituted amino acid residue(s) or other functional group(s) modified by genetic engineering or biochemical reaction. These modifications alter the speed of bioavailability through modification of the pharmacological, pharmacokinetic and pharmacodynamic properties of the insulin molecule, such as insulin glargine, insulin aspart, insulin lispro, etc.

Insulin aspart (U.S. Pat. Nos. 5,618,913, 5,547,930, 5,834,422) is a fast-acting insulin analog that demonstrates monomer stability with rapid dissociation and absorption after subcutaneous injection. In insulin aspart, the $B_{28}$ proline of a natural insulin is replaced by aspartic acid, which enhances charge repulsion and further prevents the formation of hexamers. Therefore, insulin aspart has a more rapid onset and a shorter duration of efficacy compared with normal human insulin. Further, insulin aspart has a low binding level to plasma proteins, such that the insulin aspart is eliminated from the blood faster than regular human insulin (Nosek L. et al., Diabetes, Obesity and Metabolism 15: 77-83, 2013 and Sanlioglu A D et al., Clinical utility of insulin and insulin analogs. Islets 5 (2): 67-78, 2013.).

In mammals, insulin is synthesized, processed, and stored in pancreatic (β-cells. The human insulin gene is located on the short arm of chromosome 11. The messenger RNA of insulin is translated into a single-chain polypeptide precursor of 109 amino acids, called preproinsulin. Preproinsulin contains a signal peptide of 23 amino acids. During the transfer to the rough endoplasmic reticulum, the signal peptide of preproinsulin is removed to form proinsulin. Proinsulin is composed of three parts: the amino terminal B chain (30 amino acids), the hydroxyl terminal A chain (23 amino acids), and the intermediate connecting peptide called C-peptide (35 amino acids). In the endoplasmic reticulum, proinsulin folds into its natural conformation, forming three disulfide bonds. The correctly folded proinsulin is transported to the Golgi apparatus and packaged into secretory granules. In the Golgi apparatus, proinsulin undergoes proteolytic hydrolysis to produce active insulin composed of two peptide chains, A chain and B chain. The A chain and the B chain are connected by two disulfide bonds and release the C-peptide into a free peptide fragment. The restricted cleavage sites of C-peptide are located in two basic sequences (lysine 64, arginine 65 and arginine 31, arginine 32). After the C-peptide is removed by enzyme digestion, and then the residue of arginine 31 was removed by carboxypeptidase. When cells are stimulated, mature insulin, together with C-peptide, is secreted into the blood circulation to regulate blood sugar. (Steiner D F. In. *Pancreatic Beta Cell in Health and Disease.* Pp 31-49, 2008.). The biological activity of proinsulin is only 10% of insulin.

Human insulin was the first protein drug produced by recombinant DNA technology. The first successful expression of human insulin in laboratory was announced in 1978 and recombinant human insulin was approved as a therapeutic drug in 1982. The precursor protein of the recombinant human insulin is synthesized by genetically modified organisms and proteolytically cleaved to generated active insulin. Almost all insulin analogs sold in public are modified from the insulin human gene using genetic engineering techniques and produced in *Escherichia coli* (*E. coli*) or yeast. The synthesis of recombinant human insulin has been accomplished using the following methods. For example, methods that use *Escherichia coli* expression system, either expressing a large fusion protein in the cytoplasm (Rich, D. H. et al., Pierce Chemical Company, Rockford. Pp. 721-728, 1981. and Frank, B. H. et al., Pierce Chemical Company, Rockford. Pp. 729-738, 1981.), or using a signal peptide to enable secretion into the periplasmic space (Chan, S. J. et al., *Proc. Natl. Acad. Sci. USA.* 78 (9):5401-5404, 1981.). A method that utilizes yeast, especially *Saccharomyces cerevisiae,* to express and secrete the insulin precursor has also been reported (Thim, L. et al., *Proc. Natl. Acad. Sci. USA.* 83:6766-6770, 1986.).

For methods using genetically modified *E. coli*, one method expresses the A-chain and B-chain of insulin separately in *E. coli*, and then mixes the sulfonated A-chain and B-chain to form inter-chain disulfide bonds in vitro (Rich, D. H. et al., Pierce Chemical Company, Rockford. Pp. 721-728, 1981; and Frank, B. H. et al., Pierce Chemical Company, Rockford. Pp. 729-738, 1981.). However, there are drawbacks to this method because it requires two separate fermentation processes and to form correct disulfide bonds. The inappropriate disulfide bond formation between the sulfonated A-chain and B-chain results in a low yield of insulin. Overall, the production efficiency is low.

An improved method, which expresses proinsulin with a large fusion "ballast" (Chang, S. G. et al., *Biochem. J.* 329:631-635, 1998 and Rhodes. C. J. In: *Diabetes Mellitus: A Fundamental and Clinical Text* 3rd ed. Pp 27, 2004) has been reported. The method involves cutting the fusion protein with cyanogens bromide to obtain proinsulin, sulfonating the proinsulin and separation of the sulfonated proinsulin, refolding the sulfonated proinsulin to form correct disulfide bonds in vitro, and then cleaving the C-peptide from the product with Trypsin and carboxypeptidase B, in order to generate insulin. The large size of the fusion "ballast" peptide limits the yields and may hinder the refolding process—the fusion "ballast" is required to be removed prior to refolding could occur. Excising the large fusion protein by cyanogens bromide forms a working environment hazards and requires a high level of labor protection, hence, the said process entails the inconvenience of using laborious purification steps during the preparation.

Another method was developed by Novo Nordisk Corp., (EP0163529, U.S. Pat. No. 4,916,212) which comprises expressing proinsulin comprised of a shortened B-chain (desThr30) and A-chain linked via three amino acid residues (AAK) in yeast, and isolating insulin therefrom through the steps of: fermentation, purification, enzyme reaction, acid hydrolysis, and multi-purification. This process, however, results in an unacceptably low yield of insulin. In fact, the insulin yield provided by yeasts is relative low. The intrinsical expression levels of the yeast expression system are lower and duplication cycle of the yeast expression system are longer as compared to E. coli.

The role of the C-peptide in the folding of proinsulin is not precisely known. The two dibasic sites at both end of C-peptide proinsulin are considered essential for the conversion of proinsulin to insulin (Kroeff E P. et al., J. Chromatogr. 461: 45-61, 1989 and Frank, Chance. Munch Med. Wschr., Suppl 1:S14-20, 1983.). In the production of recombinant insulin, there is a conserved, terminal dibasic amino acid sequence which has been reported to have misdirected digestion of the proinsulin by Trypsin, which results in the presence of impurities (e.g., Arg ($A_0$)-insulin) in the reaction mixture (Wetzel, R. et al., Gene. 16: 63-71, 1981.). To remove these process impurities, additional purification steps are required, which may result in additional yield loss and make the process time consuming and expensive to perform.

Several experiments (EP0055945, EP0163529, U.S. 6,875,589) (Dixon M, Webb EC Enzymes 3rd ed, London: Longman Group Ltd., pp. 261-262, 1979.) have reported that a full-length C-peptide is not necessary for insulin refolding in vitro. One opinion is that the function of the C-peptide is connecting the A-chain and B-chain, facilitating the preproinsulin refolding and forming correct disulfide bonds. Change et al. (1998) reported that the short sequence C-peptide is more effective in the refolding process than the long sequence C-peptide. For example, U.S. Pat. No. 6,875,589 reported a novel miniature proinsulin construct, of which the C-peptide is shortened to one Arginine residue. This miniature proinsulin can be converted into insulin by using Trypsin and carboxypeptidase digestion. This process did not generate Arg ($A_0$-insulin impurities. However, the process utilizes cyanogens bromide to cut the N-terminal tag before refolding, which is inefficient, more expensive, and time consuming. In addition, this patent was limited to the use for preparation of human insulin. No evidence shows that it could be used for preparation of insulin analogs, especially for insulin aspart.

As evidenced from the above review, an unmet need exists for a more efficient and improved process that has a lower potential of process impurities and a high purification quality for pharmaceutical production of insulin aspart.

SUMMARY

The invention discloses a novel proinsulin aspart structure design that can effectively improve the preparation process of recombinant insulin, and a method for preparing insulin aspart analogs.

In order to achieve the above objective, the proinsulin aspart structure provided by the present invention contains a short C-peptide and a leading sequence, and is expressed in E. coli. The invented polypeptide sequence is refolded with the leading peptide under the correct refolding conditions. Insulin aspart is transformed by two-step digestion with Trypsin and carboxypeptidase B.

The dangerous and cumbersome step of cyanogen bromide cleavage is excluded in this new process, because the newly invented proinsulin aspart can effectively fold into its natural structure in the presence of the leading peptide.

The present invention provides a novel gene structure of proinsulin aspart for preparing insulin aspart analogs. The sequence of proinsulin aspart is shown in formula I:

Wherein,

R-$R_1$ is a leading peptide sequence, which meets the following conditions:
a. R is one part of super oxide dismutase (SOD) homolog, which comprises 63 amino acids, including the active methionine; two cysteine (C) residues are substituted by serine (S);
b. The leading peptide does not affect refolding of proinsulin aspart, and can be cleaved.
c. $R_1$ is any one of Arg and Lys $R_2$ is a C-peptide, which consists of any one amino acid, Arg or Lys;

$B_1$-$B_{27}$ denotes the amino acid sequence of native human insulin B-chain from $B_1$ to $B_{27}$;

$A_1$-$A_{21}$ denotes the A-chain of native human insulin;

$B_{28}$ is any one of aspartic acid, glutamic acid and proline, preferably aspartic acid;

$B_{29}$ is any one of lysine and proline, preferably lysine; and $B_{30}$ is any one of alanine and threonine, preferably threonine.

One aspect of the present invention is related to the DNA sequence encoding of proinsulin aspart which is described by Formula I. The DNA sequence is optimized to ensure the effective expression of proinsulin aspart in appropriate host cells.

The present invention includes linking the above-described novel DNA sequence into a suitable vector, transforming the said vector having the novel DNA sequence into the E. coli, cultivating the plasmid-introduced E. coli and inducing the expression of the novel proinsulin aspart in E. coli.

Another aspect of the present invention is related to the fed-batch fermentation and production of insulin aspart, which comprises the steps of culturing E. coli cells under conditions suitable for expression of the proinsulin aspart sequence of Formula I; The cells of E. coli was treated with lysozyme and homogenized under high pressure to obtain inclusion bodies containing proinsulin aspart; Obtaining the relatively pure inclusion bodies after washing and diluting the dissolved precursor, diluting and refolding the proinsulin aspart after dissolving; the refolded proinsulin aspart is digested with Trypsin to remove the leading peptide to obtain insulin aspart-$R_2$ intermediate; The refined insulin aspart-$R_2$ intermediate is obtained by two-step ion exchange chromatography method and one-step reverse phase preparation RP-HPLC chromatography method; After digestion of a carboxypeptidase B enzyme, a mature insulin aspart is formed; after a step of reverse-phase RP-HPLC purification again, refined insulin aspart is obtained; finally, the final insulin aspart active pharmaceutical ingredient (API) is obtained through crystallization and drying.

The present invention is related an improved proinsulin aspart sequence for preparing insulin aspart analogue. Compared to the native insulin, the $B_{28}$ amino acid in B-chain of insulin aspart analogue is modified to Asp (aspartic acid).

The improved proinsulin aspart sequence refers to a single-chain polypeptide that may be converted into the insulin aspart analogue. The sequence is composed of an N-terminal leading peptide, an insulin A chain, a modified insulin B chain and an amino acid C-peptide.

The negative effect of a shortened C-peptide and smeller molecular weight when expressing in *E. coli*, the expressed fusion protein is easy to be degraded. In order to avoid this effect, the present invention includes that a leading peptide sequence is added in the N-terminal of the novel proinsulin aspart. The ideal leading peptide sequence should have the following characteristics:
1. The leading peptide sequence should not be too long, which should not cause additional metabolic burden on the host cell and not adversely affect the fermentation process;
2. The leading peptide will not hinder the refolding of the precursor in vitro, allowing normal refolding without removing the leading peptide, which protects the degradation of proinsulin aspart and enhances the solubility;
3. The leading peptide can increase the expression of the fusion protein;
4. The leading peptide can be removed easily.

The novel proinsulin aspart describes in this invention can be converted into insulin aspart-$R_2$ (Formula I) by using Trypsin digestion process. The composition of the novel proinsulin aspart sequence as the precursor for preparation of insulin aspart provides for an improved method for producing recombinant insulin aspart analog, having fewer steps and fewer hazards in the process to promote industrial safety and process management; eliminating several time consuming, expensive purification steps, and improving the yield and purity of final product by reducing the process impurities caused by incorrect refolding and undesirable cleavages.

Accordingly, the present invention discloses a novel fusion protein construct for producing insulin aspart analog. The proinsulin aspart sequence has the Formula I:

$$R\text{-}R_1\text{-}(B_1\text{-}B_{27})\text{-}B_{28}\text{-}B_{29}\text{-}B_{30}\text{-}R_2\text{-}(A_1\text{-}A_{21})$$

Wherein,
R-$R_1$ is a leading peptide sequence, which meets the following conditions:
a. R is one part of super oxide dismutase (SOD) homolog, which comprises 63 amino acids including the active methionine; two cysteine (C) residues are substituted by serine (S).
b. This leading peptide does not affect refolding of proinsulin aspart, and can be cleaved.
c. $R_1$ is any one amino acid of Arg and Lys.
$R_2$ is a C-peptide, which consists of any one amino acid, from Arg or Lys;
$B_1$-$B_{27}$ denotes the amino acid sequence of native human insulin B-chain from $B_1$ to $B_{27}$;
$A_1$-$A_{21}$ denotes the A-chain of native human insulin;

$B_{28}$ is any one of Aspartic acid, glutamic acid and proline, preferably Asp;
$B_{29}$ is any one of Lysine and Proline preferably Lysine;
$B_{30}$ is any one of Alanine and Threonine, preferably Threonine.

In one embodiment, the R may be: MATHAVSVLKGDGPVQGIIN-FEQHESNGPVKVWGSIHGLTEGLHGFHVHEFGDN-TAGSTSAGP (SEQ ID NO: 1) or MATKAVSVLKGDGPVQGIIN-FEQKESNGPVKVWGSIKGLTEGLHGFHVHEFGDN-TAGSTSAGP (SEQ ID NO: 2). The C-terminus of the leading peptide sequence is connected to short-proinsulin aspart by one arginine residue (SEQ ID NO: 3) or a lysine residue (SEQ ID NO: 4).

In one embodiment, $R_1$ and $R_2$ may be the same amino acid, such as any one amino acid of arginine or lysine.

Natural human insulin comprises an A-chain and a B-chain, wherein the A-chain has the amino acid sequence GIVEQCCTSICSLYQLENYCN (SEQ ID NO: 5) and the B-chain has the amino acid sequence FVNQHLCGSHLVEALYLVCGERGFFYTPKT (SEQ ID NO: 6). According to this invention, the B chain in formula I is modified from natural insulin. For proinsulin aspart, the proline at position $B_{28}$ of natural insulin is replaced by aspartic acid, and $B_{27}$, $B_{29}$ and $B_{30}$ are preferably natural amino acid residues.

Natural C-peptide sequence of human insulin is RREAE-DLQVGQVELGGGPGAGSLQPLALEGSLQKR (SEQ ID NO: 7), and the C-peptide of the present invention is shortened to an arginine residue (SEQ ID NO: 8) or a lysine residue (SEQ ID NO: 9). The molecular weight of proinsulin aspart provided by the present invention is much smaller than that of human proinsulin.

The sequence of natural human proinsulin is:

```
                                          (SEQ ID NO: 10)
FVNQHLCGSHLVEALYLVCGERGFFYTPKTRREAEDLQVGQVELGGGPGA

GSLQPLALEGSLQKRGIVEQCCTSICSLYQLENYCN.
```

In addition, the artificial short B chain insulin aspart precursor sequence is connected to the A chain and the B chain with three amino acid residues (AAK) in yeast. The sequence is:

```
                                          (SEQ ID NO: 11)
FVNQHLCGSHLVEALYLVCGERGFFYTDKAAKGIVEQCCTSICSLYQLEN

YCN.
```

In one embodiment, the sequence of ($B_1$-$B_{27}$)-$B_{28}$-$B_{29}$-$B_{30}$-$R_2$-($A_1$-$A_{21}$) is one of SEQ ID NO 12 or SEQ ID NO 13; The sequence of SEQ ID NO 12 is:

```
FVNQHLCGSHLVEALYLVCGERGFFYTDKTRGIVEQCCTSICSLYQLENY

CN;
```

The sequence of SEQ ID NO 13 is:

```
FVNQHLCGSHLVEALYLVCGERGFFYTDKTKGIVEQCCTSICSLYQLENY

CN.
```

The preferred sequence of proinsulin aspart provided by the present invention includes any one of SEQ ID NO 14, SEQ ID NO 15, SEQ ID NO 16, or SEQ ID NO 17:

(1)
(SEQ ID NO: 14)
MATHAVSVLKGDGPVQGIINFEQHESNGPVKVWGSIHGLTEGLHGFHVHE

FGDNTAGSTSAGPRFVNQHLCGSHLVEALYLVCGERGFFYTDKTRGIVEQ

CCTSICSLYQLENYCN (2)
(SEQ ID NO: 15)
MATHAVSVLKGDGPVQGIINFEQHESNGPVKVWGSIHGLTEGLHGFHVHE

FGDNTAGSTSAGPKFVNQHLCGSHLVEALYLVCGERGFFYTDKTKGIVEQ

CCTSICSLYQLENYCN (3)
(SEQ ID NO: 16)
MATKAVSVLKGDGPVQGIINFEQKESNGPVKVWGSIKGLTEGLHGFHVHE

FGDNTAGSTSAGPRFVNQHLCGSHLVEALYLVCGERGFFYTDKTRGIVEQ

CCTSICSLYQLENYCN (4)
(SEQ ID NO: 17)
MATKAVSVLKGDGPVQGIINFEQKESNGPVKVWGSIKGLTEGLHGFHVHE

FGDNTAGSTSAGPKFVNQHLCGSHLVEALYLVCGERGFFYTDKTKGIVEQ

CCTSICSLYQLENYCN

This proinsulin aspart can be used as a precursor for the preparation of insulin aspart analogs in E. coli or other host cells. The improved proinsulin aspart can be converted into insulin aspart by two-step digestion with Trypsin and carboxypeptidase B. The sequence of the improved proinsulin aspart provides an improved method for the production of recombinant insulin aspart analogs.

The genetic code for the improved proinsulin aspart can be obtained as shown below. In mRNA or DNA, a group of three adjacent nucleotides, also called triads, encodes an amino acid called the genetic code. An amino acid usually has one or more genetic codes, called codon degeneracy. The following table shows the genetic code and corresponding amino acids.

| Amino acid | Codons | Amino acid | Codons |
|---|---|---|---|
| Ala/A | GCT, GCC, GCA, GCG | Leu/L | TTA, TTG, CTT, CTC, CTA, CTG |
| Arg/R | CGT, CGC, CGA, CGG, AGA, AGG | Lys/K | AAA, AAG |
| Asn/N | AAT, AAC | Met/M | ATG |
| Asp/D | GAT, GAC | Phe/F | TTT, TTC |
| Cys/C | TGT, TGC | Pro/P | CCT, CCC, CCA, CCG |
| Gln/Q | CAA, CAG | Ser/S | TCT, TCC, TCA, TCG, AGT, AGC |
| Glu/E | GAA, GAG | Thr/T | ACT, ACC, ACA, ACG |
| Gly/G | GGT, GGC, GGA, GGG | Trp/W | TGG |
| His/H | CAT, CAC | Tyr/Y | TAT, TAC |
| Ile/I | ATT, ATC, ATA | Val/V | GTT, GTC, GTA, GTG |
| START | ATG | STOP | TAA, TGA, TAG |

Codon bias refers to the degenerate usage frequency among different organisms, even in the same species for different coding genes. For efficient expression in a special host, the genetic codon selection and gene structure need to be optimized. Embodiments of the present invention include the optimized gene sequences for the novel proinsulin aspart, to ensure efficient expression of these proteins in E. coli. Preferred gene sequences of the present invention may include:

(1)
(SEQ ID NO: 18)
5'-ATGGCGACGCATGCCGTGAGCGTGCTGAAGGGCGACGGCCCAGTGCA

GGGCATCATCAATTTCGAGCAGCATGAAAGTAATGGACCAGTGAAGGTGT

GGGGAAGCATTCATGGACTGACTGAAGGCCTGCATGGATTCCATGTTCAT

GAGTTTGGAGATAATACAGCTGGCTCTACCAGTGCAGGTCCGCGGTTTGT

GAACCAGCATCTGTGCGGCAGCCATCTGGTGGAAGCGCTGTATCTGGTGT

GCGGCGAACGCGGCTTCTTTTATACCGATAAAACCCGCGGCATTGTGGAA

CAGTGCTGCACCAGCATTTGCAGCCTGTATCAGCTGGAAAACTATTGCAA

CTAA-3'

(2)
(SEQ ID NO: 19)
5'-ATGGCGACGCATGCCGTGAGCGTGCTGAAGGGCGACGGCCCAGTGCA

GGGCATCATCAATTTCGAGCAGCATGAAAGTAATGGACCAGTGAAGGTGT

GGGGAAGCATTCATGGACTGACTGAAGGCCTGCATGGATTCCATGTTCAT

GAGTTTGGAGATAATACAGCTGGCTCTACCAGTGCAGGTCCGAAATTTGT

GAACCAGCATCTGTGCGGCAGCCATCTGGTGGAAGCGCTGTATCTGGTGT

GCGGCGAACGCGGCTTCTTTTATACCGATAAAACCCGCGGCATTGTGGAA

CAGTGCTGCACCAGCATTTGCAGCCTGTATCAGCTGGAAAACTATTGCAA

CTAA3-'

(3)
(SEQ ID NO: 20)
5'-ATGGCGACGAAAGCCGTGAGCGTGCTGAAGGGCGACGGCCCAGTGCA

GGGCATCATCAATTTCGAGCAGAAAGAAAGTAATGGACCAGTGAAGGTGT

GGGGAAGCATTAAAGGACTGACTGAAGGCCTGCATGGATTCCATGTTCAT

GAGTTTGGAGATAATACAGCTGGCTCTACCAGTGCAGGTCCGCGGTTTGT

GAATCAGCATCTGTGCGGCAGCCATCTGGTGGAAGCGCTGTATCTGGTGT

GCGGCGAACGCGGCTTCTTTTATACCGATAAAACCCGCGGCATTGTGGAA

CAGTGCTGCACCAGCATTTGCAGCCTGTATCAGCTGGAAAATTATTGCAA

CTAA-3'

(4)
(SEQ ID NO: 21)
5'-ATGGCGACGAAAGCCGTGAGCGTGCTGAAGGGCGACGGCCCAGTGCA

GGGCATCATCAATTTCGAGCAGAAAGAAAGTAATGGACCAGTGAAGGTGT

GGGGAAGCATTAAAGGACTGACTGAAGGCCTGCATGGATTCCATGTTCAT

GAGTTTGGAGATAATACAGCTGGCTCTACCAGTGCAGGTCCGAAATTTGT

GAATCAGCATCTGTGCGGCAGCCATCTGGTGGAAGCGCTGTATCTGGTGT

GCGGCGAACGCGGCTTCTTTTATACCGATAAAACCCGCGGCATTGTGGAA

CAGTGCTGCACCAGCATTTGCAGCCTGTATCAGCTGGAAAATTATTGCAA

CTAA-3'

The present invention includes inserting the above-described optimized DNA sequence into a suitable expression vector and transforming to suitable host cells. Proper fermentation conditions are optimized to achieve high level of expression.

The expression vector mentioned in the present invention comprising the above nucleotide sequence is the vehicle that carries and expresses a foreign gene into the cells, generally refers to the DNA plasmid. The recombinant expression vector is preferably proinsulin aspart plasmid for expression by T7 RNA polymerase (pET)-API. The pET expression system, developed in 1986, is widely used for its ability to mass-produce proteins using the T7 promoter (which only binds T7 RNA polymerase) and allows those skilled in art to manipulate expression of a desired protein and the timing of that expression. A number of pET plasmids are commercially available and those of ordinary skill in the art can and do routinely create custom pET plasmids. The expression plasmid must carry cis-acting components, such as a promoter region, the transcription initiation site, a ribosome binding site and other DNA sequences, and usually carry an antibiotic resistance gene for positive selection, such as B-lactamase gene (ampicillin resistance), neomycin phosphotransferase enzyme (kanamycin resistance), etc. The expression plasmid carrying the target gene can be transformed into suitable host cells by chemical or physical methods, then select the positive clones by antibiotic resistance.

The expression host cells mentioned in the present invention means any cells that can express exogenous genes, including mammalian cells, insect cells, yeast and a variety of prokaryotic cells. The preferred host cells are prokaryotic cells that may be any natural bacteria, such as *Escherichia coli, Bacillus subtilis, Salmonella*, or it can be any modified strains that are more suitable for recombinant protein expression, such as *E. coli* DH5a, K12JM107, W3110, BL21(DE3), Rosetta, and other strains. Such host cells or microorganisms contain the above-mentioned expression vector. The host cell or microorganism is preferably *Escherichia coli* containing the proinsulin aspart pET-API recombinant expression vector.

According to the embodiments, the methods of producing insulin aspart described herein generally include the following steps:
1. Design and construct the proinsulin aspart sequence according to Formula I;
2. Fermentation and expression of the proinsulin aspart;
3. Isolation and solubilization of inclusion body, as well as refolding of proinsulin aspart;
4. Enzymatic conversion of proinsulin aspart to insulin aspart-$R_2$ intermediate;
5. Purification of insulin aspart-$R_2$ intermediate;
6. Enzymatic conversion of insulin aspart-$R_2$ intermediate to mature insulin aspart;
7. And after crystallization and drying, the insulin aspart API is obtained.

Figure 1:
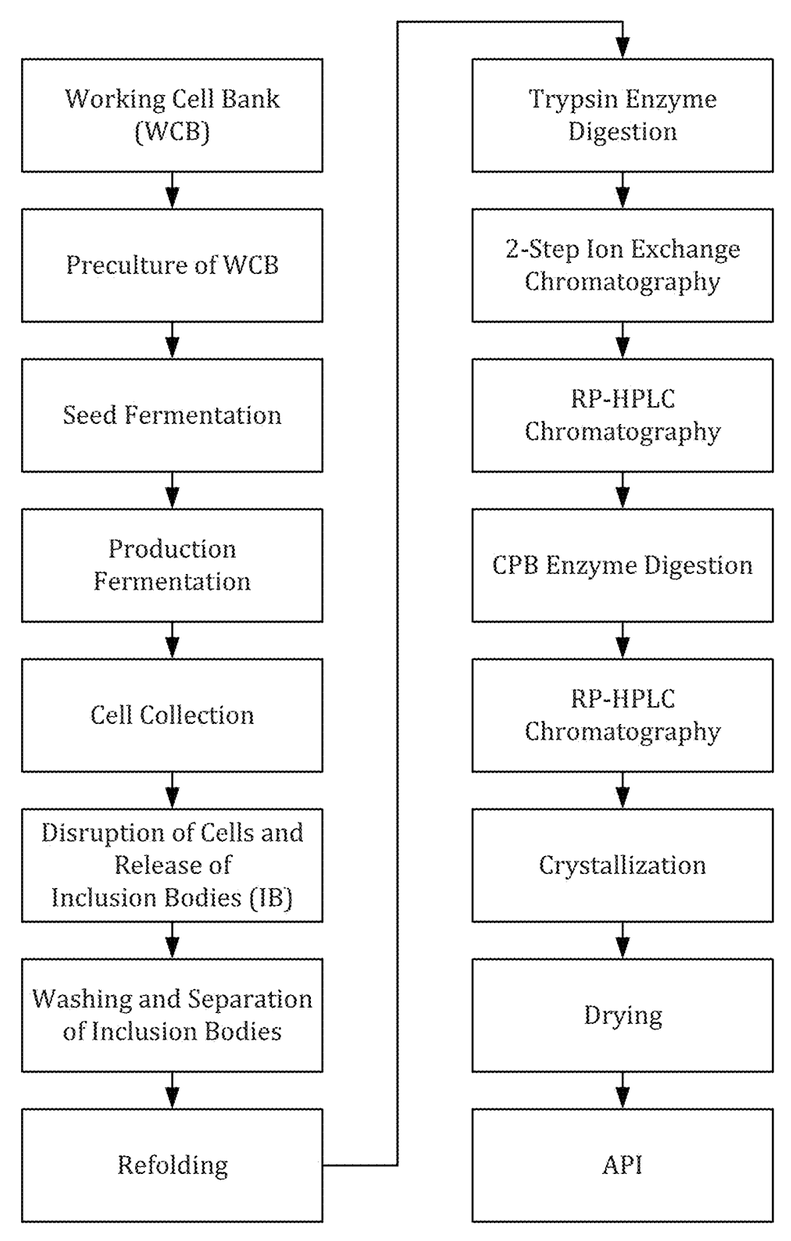
FIG. 1 is a process flow diagram of the preparation of insulin aspart using an improved proinsulin aspart in *Escherichia coli*.

FIG. 1 illustrates the schematic flow chart of the preferred process steps in producing insulin aspart analog according to embodiments of the present invention.

One embodiment of the present invention is SEQ ID NO: 14. In a preferred embodiment, the sequence is SEQ ID NO: 15. In another preferred embodiment, the sequence is SEQ ID NO: 16. In another preferred embodiment, the sequence is SEQ ID NO: 17.

In one embodiment, the above-optimized gene is inserted into a suitable vector, such as PTAC expression plasmid series, pGEX series or PET pET series, preferably PET pET series plasmids, and more preferably plasmid pET-28a (which can be obtained commercially from NOVAGEN® (Product No. 69864)); This expression plasmid can transfect K12 JM109 engineered strain or K12 W110 engineered strains to form the expression clone. In another preferred embodiment, the expression plasmid is transfected into BL21 (DE3) engineered strains. This expression clone can be cultivated by shake-flask or fermenter to a proper concentration. The expression of proinsulin aspart can then be induced. The cells that contain the expressed proinsulin aspart as inclusion bodies can be collected by centrifugation.

The cells that contain inclusion bodies of proinsulin aspart are lysed by lysozyme treatment and homogenization. The isolated inclusion bodies are washed by a solution containing detergent or a low-concentration chaotropic reagent and solubilized with solution buffer by high pH. In one embodiment, the solution buffer contains Tris, EDTA and L-cysteine. The concentration of Tris is about 10-50 mM, the concentration of EDTA is about 0.05-1.00 mM and the concentration of L-cysteine is about 0.25-5.0 mM; more preferably, the concentration of Tris concentration is about 20-30 mM; the concentration of EDTA is about 0.05-0.25 mM and the concentration of L-cysteine is about 0.25-1.0 mM. When dissolved, the pH of the solution is about 11.6-12.4, preferably, about 11.8-12.2; the temperature of the solution is about 10-30° C., preferably, 15-25° C. It may take about 10-120 min to dissolve the inclusion bodies, preferably, 10-60 min. The proinsulin aspart will be refolded. In one embodiment, the pH of solution is about 10.0-11.6, preferably, about 10.8-11.4; the temperature of solution is about 10-25° C., preferably, about 15-20° C.; the concentration of total protein is about 1-10 g/L, preferably, about 1-7 g/L; the duration of refolding is about 12-48 hours, preferably, about 24-36 hours.

In one embodiment, the Trypsin is added into the refolded proinsulin aspart for digestion. The pH of Trypsin digestion is about 8.0-10.0, preferably, about 8.5-9.5; the concentration of Trypsin is about 0.025-0.12.5 mg/L protein, preferably, about 0.050-0.083 mg/L protein; the temperature of digestion is about 15-37° C., preferably, about 18-25° C.; the duration of digestion is about 24-48 hours, preferably, about 24-40 hours. After the digestion is finished, a final concentration of 3 mM zinc is added to the digestion solution of the Trypsin. The solution pH is adjusted to 6.0. This allows insulin aspart-$R_2$ intermediate product to form a flocculent precipitate. The insulin aspart-$R_2$ precipitate can be resolubilized in appropriate buffer and purified by proper method to obtain the insulin aspart-$R_2$ intermediate product.

In one embodiment, the insulin aspart-$R_2$ solution is purified by $1^{st}$ SP cation column chromatography to reach a product purity of about 80% and followed by $2^{st}$ SP cation column to reach a product purity of about 85%. Further purification may be performed with reverse phase preparation to remove impurities. The final insulin aspart-$R_2$ product can reach a 95% or higher purity and the content of impurities DesB30-insulin aspart is reduced to below 0.1%. In another better embodiment, the insulin aspart-$R_2$ solution is purified directly by preparative HPLC-RP. The final insulin aspart-$R_2$ product can reach a purity of 95% or higher purity. In one embodiment, use preparative HPLC-RP with ammonium sulfate buffer system for $3^{rd}$ column separation, wherein the concentration of ammonium sulfate ranges from 0.1 to 0.3 M, more preferably, 0.15-0.2 M; the pH is in the range of 2.0-4.0; and the organic modifier can be ethanol, methanol or acetonitrile. The insulin aspart-$R_2$ is eluted with a linear concentration gradient of the organic solvent. In another better embodiment, use preparative HPLC-RP with sodium sulfate buffer system for $3^{rd}$ column separation, wherein the concentration of sodium sulfate ranges from 0.1 to 0.3 M, more preferably, 0:15-0.2 M; the pH is in the range of 2.0-4.0; and the organic modifier can be ethanol, methanol or acetonitrile. The insulin aspart-$R_2$ is eluted with a linear concentration gradient of the organic solvent. In another preferred embodiment, use the preparative HPLC-RP with mixed sodium acetate and ammonium acetate plating buffer system for purification, wherein the concentration of sodium acetate ranges from 0.1 to 0.3 M, more preferably 0.15-0.2 M; the concentration of the ammonium acetate ranges from 0.1 to 0.3 M, more preferably 0.15-0.2 M; the pH is in the range of 2.0-4.0; and the organic modifier can be ethanol, methanol or acetonitrile. The insulin aspart-$R_2$ is eluted with a linear concentration gradient of the organic solvent.

After the $3^{rd}$ column separation, insulin aspart-$R_2$ is converted into insulin aspart by carboxypeptidase B. Firstly, dissolve the insulin aspart-$R_2$ intermediate with solubilization buffer. In one embodiment, the solution contains Tris and EDTA. The concentration of Tris is about 10-100 mM and the concentration of EDTA is about 1-4 mM; more preferably, the concentration of Tris concentration is about 20-30 mM and the concentration of EDTA is about 2-4 mM. The insulin aspart-$R_2$ is dissolved at pH 9.0. After dissolution, the carboxypeptidase B(CPB) is added into the dissolution solution. In one embodiment, the concentration of carboxypeptidase B is about 0.2-1.0 mg/g protein, preferably, about 0.25-0.5 mg/g protein; the pH of carboxypeptidase B digestion is about 8.0-10.0, preferably, about 8.0-9.0; the temperature of carboxypeptidase B digestion is about 20-37° C., preferably, about 20-30° C.; the concentration of total protein is about 4-7 g/L, preferably, about 4-6 g/L; the duration of carboxypeptidase B digestion is about 3-24 hours, preferably, about 3-15 hours.

The mature insulin aspart solution after carboxypeptidase B digestion is purified by preparative HPLC-RP to reach a product purity of about 99%. In one embodiment, use preparative HPLC-RP with ammonium sulfate buffer system for $4^{th}$ column separation, wherein the concentration of ammonium sulfate ranges from 0.1 to 0.3 M, more preferably, 0.15-0.2 M; the pH is in the range of 2.0-4.0; and the organic modifier can be ethanol, methanol or acetonitrile. The insulin aspart is eluted with a linear concentration gradient of the organic solvent. In another preferred embodiment, use the preparative HPLC-RP with sodium sulfate buffer system for $4^{th}$ column separation, wherein the concentration of sodium sulfate ranges from 0.1 to 0.3 M, more preferably 0.15-0.2 M; the pH is in the range of 2.0-4.0; and the organic modifier can be ethanol, methanol or acetonitrile. The insulin aspart is eluted with a linear concentration gradient of the organic solvent. In another more preferred embodiment, use the preparative HPLC-RP with mixed sodium acetate, ammonium acetate and Tris buffer system for final purification, wherein the concentration of sodium acetate ranges from 0.05 to 0.3 M, more preferably 0.1-0.12 M; the concentration of ammonium acetate ranges from 0.05 to 0.3 M, more preferably 1-0.2 M; the concentration of Tris ranges from 0.05 to 0.3 M, more preferably 0.075-0.2 M; the pH is in the range of 7.1-8.5; and the organic modifier can be ethanol, methanol or acetonitrile. The insulin aspart is eluted with a linear concentration gradient of the organic solvent.

In one embodiment, insulin aspart eluted from HPLC-RP is precipitated with 3-7 mM zinc chloride, and the precipitate is collected. The collected precipitate is dissolved with 5-20 mM hydrochloric acid solution, and the concentration of insulin aspart is adjusted to 3-15 mg/mL. Add sodium chloride with a final concentration of 50-200 mM, trisodium citrate dihydrate with a final concentration of 20-100 mM, 0.2%-1.0% (v/v) m-cresol and 10-30% (v/v) absolute ethanol, into insulin aspart solution and adjust pH to 6.0-6.3. Finally, add zinc acetate with a final concentration of 6 mM to the solution, stir at room temperature for 2-3 hours and then place it at 10-20° C. for 20-24 h. After the crystallization is completed, each gram of insulin aspart is washed with 75%-100% ethanol solution, and the crystals are collected after washing; each gram of insulin aspart is washed again with 5-10 mL of absolute ethanol, and the crystals are collected after washing. Transfer the crystals to a vacuum drying oven, and dry them at 15-35° C. for 60-96 h. Otherwise, the vacuum pressure is not greater than −0.08 MPa.

This insulin aspart active pharmaceutical ingredient (API) final obtained by the preparation process described in the present invention is in the form of crystals.

The advantage of using the improved proinsulin aspart sequence as a precursor to produce insulin aspart is that the *E. coli* fusion SOD homologue is used for expression in this process, and a single amino acid is used as the C peptide, which effectively avoids impurity problem of Arg (A0)-insulin, makes the purification process easier and removes some time-consuming and expensive purification steps; because C-peptide is only one amino acid, it reduces the quality loss of the enzyme conversion step; improve the yield and purity of the final product by reducing impurities caused by wrong refolding and wrong digestion process; compared with the yeast expression system in the prior art, the inclusion body expression of *Escherichia coli*, alkali dissolution and renaturation are adopted in this patent application, which can obtain a higher yield and greatly shorten the fermentation period; the development of Trypsin digestion promotes the maturation of insulin aspart molecules, avoids the use of highly toxic and dangerous reagent cyanogen bromide, improves the operability of the process and provides a safe working environment. Therefore, the production cost of preparing high-quality insulin aspart can be greatly reduced.

BRIEF DESCRIPTION OF THE DRAWINGS

According to the present invention.

DESCRIPTION OF THE EMBODIMENTS

Detailed Ways

In order to facilitate those skilled in the art to understand the content of the present invention, the technical solutions of the present invention will be further described below in conjunction with specific embodiments, but the following content should not limit the scope of protection claimed by the claims of the present invention in any way.

The materials and reagents used in the following examples can be obtained from commercial sources unless otherwise specified.

Example 1: Construction of an *E. coli* Clone Expressing Proinsulin Aspart of Formula I A proinsulin aspart fusion protein sequence, such as Formula I, is designed for expression in *E. coli*. The N terminal leading amino acid sequence can enhance expression and protect proinsulin aspart from degradation by *E. coli*. The preferred leading amino acid sequence is (SEQ ID NO: 1)
MATHAVSVLKGDGPVQGIINFEQHESNGPVKVWGSIHGLTEGLHGFHVHE

FGDNTAGSTSAGP;

The C terminal of this leading amino acid sequence is connected to the B-chain of the insulin aspart by an arginine or lysine residue, which enable the cleavage of the leading peptide by Trypsin at the same time. The C-peptide of the proinsulin aspart is shortened to a single arginine or lysine residue, and the precursor sequence of the novel proinsulin aspart sequence, is:

(SEQ ID NO: 2)
FVNQHLCGSHLVEALYLVCGERGFFYTDKTRGIVEQCCTSICSLYQLENY

CN.

The full length of proinsulin aspart with leading peptide is MATHAVSVLKGDGPVQGIIN-FEQHESNGPVKVWGSIHGLTEGLHGFHVHEFGDN-TAGSTSAGPRFVNQHLCGSHLVEALYL-VCGERGFFYTDKTRGIVEQCCTSICSLYQLENYCN (SEQ ID NO: 14). To ensure efficient expression of the protein of SEQ ID NO: 14 in *E. coli*, the genetic codons are optimized. The optimized gene sequences are:

(SEQ ID NO: 18)
5'ATGGCGACGCATGCCGTGAGCGTGCTGAAGGGCGACGGCCCAGTGCAG

GGCATCATCAATTTCGAGCAGCATGAAAGTAATGGACCAGTGAAGGTGTG

GGGAAGCATTCATGGACTGACTGAAGGCCTGCATGGATTCCATGTTCATG

AGTTTGGAGATAATACAGCTGGCTCTACCAGTGCAGGTCCGCGGTTTGTG

AACCAGCATCTGTGCGGCAGCCATCTGGTGGAAGCGCTGTATCTGGTGTG

CGGCGAACGCGGCTTCTTTTATACCGATAAAACCCGCGGCATTGTGGAAC

AGTGCTGCACCAGCATTTGCAGCCTGTATCAGCTGGAAAACTATTGCAAC

TAA3'.

A DNA fragment of SEQ ID NO: 18 is chemically synthesized by commercial CRO company. A 5' NcoI site: CCATGG and 3' Hind III site: AAGCTT are included in the synthesized DNA fragment. The DNA fragment encoding the entire amino acid sequence of SEQ ID NO: 14 is cleaved with the Nco I and Hind III restriction enzymes and inserted into the pET 28a expression vector, which is digested with the same restriction enzymes, to form the pET-API expression vector.

The transformed pET-API expression vectors are transfected into *E. coli* strain BL21 (DE3). The positive clones are selected by Kanamycin resistance and confirmed by DNA sequencing. The confirmed positive clone is cultured and amplified. Sterile medium and glycerol are added to the cells. One (1) ml aliquots of the cells are then dispensed into sterile ampoules and stored at −80° C., forming the proinsulin aspart working cell bank (WCB).

Example 2: Expression of the Proinsulin Aspart Fusion Protein

Culture the cells from the WCB of Example 1 in LB media (containing 1.5% w/v yeast extract, and 0.5% w/v NaCl) at 37° C. for 8 hours to obtain the cell seeds solution. The recovered seeds solution are inoculated into BFM media (containing 0.6% w/v $(NH_4)_2HPO_4$, 0.4% w/v $NH_4Cl$, 1.35% w/w $KH_2PO_4$, 0.139% w/w $MgSO_4.7H_2O$, 0.28% w/w Citric Acid Monohydrate, 0.8% w/w Glucose, 0.3% w/w Yeast Extract Powder and 1% mL/L Trace Element Solution) to further culture for another 8 hours to obtain a second generation of seeds, which is then inoculated into fermentor in a volume ratio of 1:10. Culture for about 16 hours until the $O.D_{600}$ (optical density) of the fermentation liquor reaches about 150. Then, add 1 mM IPTG to the fermentor to induce proinsulin aspart expression. Incubate for another 12 hours to finish the fermentation. The cells are collected by centrifugation.

The harvested cells, containing inclusion bodies of proinsulin aspart, are suspended in 25 mM Tris, 10 mM EDTA, pH 8.0 buffers, with a cell concentration of 200 g/L. The cells are lysed by lysozyme treatment and homogenization. Discard the supernatant of lysed cells and collect the inclusion body pellet.

Wash the inclusion bodies pellet with a buffer of 25 mM Tris, 1M Urea, 1% Tween 20, pH 8.0. Resuspend the washed inclusion bodies in a buffer of 25 mM Tris, 0.1 M EDTA and 0.5 mM L-cysteine pH is adjusted to 12 and keep the solution dissolved at 15-25° C. for 10-60 min. The solution is named the inclusion bodies dissolution solution.

Example 3: Refolding of the Proinsulin Aspart

After dissolution the inclusion body solution was filtered with a 1 μm PP filter element, the temperature was controlled to 20° C., the pH was adjusted to 11.0, and then refolded for 24-48 h to obtain refolded proinsulin aspart.

Example 4: Transformation and Purification of Trypsin Enzyme Digestion

When the refolding is complete, adjust the solution pH to 9.0. Add Trypsin to the final concentration of 0.063 mg/g protein to the refolded protein solution. Digest at 18° C. for 36 hours to cleave the leading peptides, to obtain B31Arg-insulin aspart intermediate. The process can be monitored by HPLC-RP (C18). After digestion is finished, a final concentration of 3 mM zinc is added to the solution, and the pH is adjusted to 6.0. A flocculent precipitate of B31Arg-insulin aspart is formed.

The B31Arg-insulin aspart precipitate is dissolved in a buffer of 3% isopropanol and 50 mM acetic acid, at pH 3.5. The dissolved B31Arg-insulin aspart solution is loaded onto a SP column as sample, which has been equilibrated with the same buffer for dissolving the insulin aspart. The B31Arg-insulin aspart can also be eluted by 30% isopropanol, 1 M sodium chloride in linear gradient. After two SP chromatography purifications, the purity of B31Arg-insulin aspart is about 85%. The B31Arg-insulin aspart eluate was added with 5 mM zinc chloride and the pH was adjusted to 6.5 to form a flocculated precipitate of B31Arg-insulin aspart.

Further purification can be performed with reverse phase preparation to remove impurities. The final purity of B31Arg-aspart insulin can reach more than 98%, and the content of DesB30-insulin aspart drops below 0.1%. That high-purity B31Arg-aspart insulin intermediate is obtained.

Example 5: Transformation of Carboxypeptidase B Enzyme Digestion

The purified B31Arg-insulin aspart intermediate precipitate was resuspended in 25 mM Tris and 2 mM EDTA, and dissolved at the pH 9.0. After the dissolution is completed, adjust the pH of the solution to 8.5 and add the final concentration of 0.33 mg/g protein to the dissolution solution to conduct enzyme digestion at 20° C. for 3 h. After that, the C-peptide arginine residue was removed to obtain insulin aspart. This process can be detected by HPLC-RP (C18). Otherwise, after the digestion is completed, the pH of the digestion solution is adjusted to 3.8, and the digestion is terminated.

Example 6: Final Purification and Freeze-Dry

Loading the converted insulin aspart onto the reverse phase preparative chromatography column and equilibrate the column with a solution obtained by mixing 0.1M ammonium acetate, 0.1M sodium acetate, 0.1 M Tris and pH 7.5 with acetonitrile a ratio of 9:1. The elution buffer is a solution obtained by mixing a solution of 0.1 M ammonium acetate, 0.1 M sodium acetate, 0.1 M Tris and pH 3.5 with acetonitrile in a ratio of 1:9. In addition, insulin aspart is eluted with a linear gradient of elution buffer.

Zinc chloride with a final concentration of 5 mM was added to the insulin aspart solution in the reverse phase preparation eluate, to form a precipitate. In order to control the concentration of insulin aspart to 8 mg/ml, the precipitate is dissolved in 10 mM hydrochloric acid solution. Add the final concentration of 150 mM NaCl, 50 mM trisodium citrate, 0.5% (v/v) m-cresol and 20% (v/v) absolute ethanol to the insulin aspart solution, and adjust the pH to 6.3. Finally, add zinc acetate with a final concentration of 6 mM to the solution and then leave it at 15° C. for 24 hours after stirring at room temperature for about 3 h. After crystallization is completed, the crystals are collected by suction filtration. Then use 5 ml 75% ethanol solution/(g insulin aspart) to clean the crystals, and collect the crystals after washing. Wash the crystals again with 10 ml ethanol solution/(g insulin aspart), and collect the crystals after washing. Finally, the crystals are transferred to a vacuum drying oven and dried at a temperature of 25° C. for 80 h, and the vacuum pressure is not greater than −0.08 MPa. After drying, the final insulin aspart API is obtained.

What is claimed is:

1. A novel short-proinsulin aspart sequence for preparing recombinant insulin aspart and analogs thereof, wherein the sequence has an amino acid sequence as shown in Formula I:

$R\text{-}R_1\text{-}(B_1\text{-}B_{27})\text{-}B_{28}\text{-}B_{29}\text{-}B_{30}\text{-}R_2\text{-}(A_1\text{-}A_{21})$, wherein R-$R_1$ is a leading peptide sequence, which meets the following conditions:
(a) R is one part of super oxide dismutase (SOD) homolog, which consists of 63 amino acids including active methionine; and two cysteine (C) residues are substituted by serine(S);
wherein, the sequence of R is SEQ ID NO: 1:

MATHAVSVLKGDGPVQGIINFEQHESNGPVKVWGSIHGLTEGLHGFHVHE

FGDNTAGSTSAGP;

(b) the leading peptide does not affect refolding of short-proinsulin aspart and can be cleaved;
(c) $R_1$ is any one of Arg and Lys,
$R_2$ is a C-peptide, which consists of any one from Arg or Lys;
$B_1$-$B_{27}$ denotes an amino acid sequence of B1 to B27 in B-chain of native human insulin;
$A_1$-$A_{21}$ denotes an A-chain of native human insulin;
$B_{28}$ is Aspartic acid;
$B_{29}$ is Lysine; and
$B_{30}$ is Threonine;
the sequence of ($B_1$-$B_{27}$)-$B_{28}$-$B_{29}$-$B_{30}$-$R_2$-($A_1$-$A_{21}$) is one of SEQ ID NO: 12 or SEQ ID NO: 13;
a sequence of SEQ ID NO: 12 is:
FVNQHLCGSHLVEALYLVCGERGFFYTDKTR-GIVEQCCTSICSLYQLENYCN; and
a sequence of SEQ ID NO: 13 is:

FVNQHLCGSHLVEALYLVCGERGFFYTDKTKGIVEQCCTSICSLYQLENY

CN.

2. The proinsulin aspart sequence according to claim 1, wherein $R_1$ and $R_2$ are both arginine or both lysine.

3. The proinsulin aspart sequence according to claim 1, wherein the proinsulin aspart sequence is one of SEQ ID NO: 14 or SEQ ID NO: 15;

a sequence of SEQ ID NO: 14 is:

MATHAVSVLKGDGPVQGIINFEQHESNGPVKVWGSIHGLTEGLHGFHVHE

FGDNTAGSTSAGPRFVNQHLCGSHLVEALYLVCGERGFFYTDKTRGIVEQ

CCTSICSLYQLENYCN;

and
a sequence of SEQ ID NO 15: is:

MATHAVSVLKGDGPVQGIINFEQHESNGPVKVWGSIHGLTEGLHGFHVHE

FGDNTAGSTSAGPKFVNQHLCGSHLVEALYLVCGERGFFYTDKTKGIVEQ

CCTSICSLYQLENYCN.

4. A nucleic acid sequence, wherein the nucleic acid sequence encodes the proinsulin aspart sequence of claim 1.

5. A recombinant expression vector, wherein the recombinant expression vector comprises the nucleic acid sequence of claim 4.

6. The recombinant expression vector according to claim 5, wherein the expression vector is proinsulin aspart pET-active pharmaceutical ingredient (pET-API).

7. A microorganism, wherein the microorganism comprises the recombinant expression vector of claim 5.

8. The microorganism according to claim 7, wherein the microorganism is *E. coli*, and the expression vector is proinsulin aspart pET-API.

9. A process for preparing insulin aspart, comprising following steps:
(a) culturing *E. coli* cells under conditions suitable for expressing the short-proinsulin aspart sequence of the Formula I of claim 1;
(b) disrupting the cultured *E. coli* cells to provide inclusion bodies containing the short-proinsulin aspart sequence of claim 1;
(c) solubilizing and refolding the inclusion bodies;
(d) enzymatically cleaving the refolded proinsulin aspart to be converted into insulin aspart-$R_2$ intermediates with an initial purity;
(e) purifying insulin aspart-$R_2$ intermediates by a two-step ion exchange chromatography and a one-step RP-HPLC chromatography to obtain insulin aspart-$R_2$ intermediates with a final purity, wherein the final purity is higher than the initial purity;
(f) converting the insulin aspart-$R_2$ intermediates having the final purity from step (e) with carboxypeptidase B to obtain mature insulin aspart;

(g) further purifying the mature insulin aspart using the RP-HPLC chromatography to obtain insulin aspart with high purity after carboxypeptidase B digestion; and (h) drying and crystallizing insulin aspart with high purity to form a final API of insulin aspart.

* * * * *

SEQUENCE LISTING

```
<160> NUMBER OF SEQ ID NOS: 21

<210> SEQ ID NO 1
<211> LENGTH: 63
<212> TYPE: PRT
<213> ORGANISM: Artificial sequence
<220> FEATURE:
<223> OTHER INFORMATION: Synthesized

<400> SEQUENCE: 1

Met Ala Thr His Ala Val Ser Val Leu Lys Gly Asp Gly Pro Val Gln
1               5                   10                  15

Gly Ile Ile Asn Phe Glu Gln His Glu Ser Asn Gly Pro Val Lys Val
            20                  25                  30

Trp Gly Ser Ile His Gly Leu Thr Glu Gly Leu His Gly Phe His Val
        35                  40                  45

His Glu Phe Gly Asp Asn Thr Ala Gly Ser Thr Ser Ala Gly Pro
    50                  55                  60

<210> SEQ ID NO 2
<211> LENGTH: 63
<212> TYPE: PRT
<213> ORGANISM: Artificial sequence
<220> FEATURE:
<223> OTHER INFORMATION: Synthesized

<400> SEQUENCE: 2

Met Ala Thr Lys Ala Val Ser Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Ser Thr Ser Ala Gly Pro
    50                  55                  60

<210> SEQ ID NO 3
<211> LENGTH: 1
<212> TYPE: PRT
<213> ORGANISM: Artificial sequence
<220> FEATURE:
```

```
<223> OTHER INFORMATION: Synthesized

<400> SEQUENCE: 3

Arg
1

<210> SEQ ID NO 4
<211> LENGTH: 1
<212> TYPE: PRT
<213> ORGANISM: Artificial sequence
<220> FEATURE:
<223> OTHER INFORMATION: Synthesized

<400> SEQUENCE: 4

Lys
1

<210> SEQ ID NO 5
<211> LENGTH: 21
<212> TYPE: PRT
<213> ORGANISM: Homo sapiens
<220> FEATURE:
<223> OTHER INFORMATION: Native human insulin A chain

<400> SEQUENCE: 5

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 6
<211> LENGTH: 30
<212> TYPE: PRT
<213> ORGANISM: Homo sapiens
<220> FEATURE:
<223> OTHER INFORMATION: Native human insulin B chain

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 7
<211> LENGTH: 35
<212> TYPE: PRT
<213> ORGANISM: Homo sapiens
<220> FEATURE:
<223> OTHER INFORMATION: Native human insulin C peptide

<400> SEQUENCE: 7

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 8
<211> LENGTH: 1
<212> TYPE: PRT
<213> ORGANISM: Artificial sequence
<220> FEATURE:
<223> OTHER INFORMATION: Synthesized
```

```
<400> SEQUENCE: 8

Arg
1

<210> SEQ ID NO 9
<211> LENGTH: 1
<212> TYPE: PRT
<213> ORGANISM: Artificial sequence
<220> FEATURE:
<223> OTHER INFORMATION: Synthesized

<400> SEQUENCE: 9

Lys
1

<210> SEQ ID NO 10
<211> LENGTH: 86
<212> TYPE: PRT
<213> ORGANISM: Homo sapiens
<220> FEATURE:
<223> OTHER INFORMATION: Native human proinsulin

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 11
<211> LENGTH: 53
<212> TYPE: PRT
<213> ORGANISM: Artificial sequence
<220> FEATURE:
<223> OTHER INFORMATION: Synthesized

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Ala Ala Lys
            20                  25                  30

Gly Ile Val Glu Gln Cys Cys Thr Ser Ile Cys Ser Leu Tyr Gln Leu
        35                  40                  45

Glu Asn Tyr Cys Asn
    50

<210> SEQ ID NO 12
<211> LENGTH: 52
<212> TYPE: PRT
<213> ORGANISM: Artificial sequence
<220> FEATURE:
<223> OTHER INFORMATION: Synthesized

<400> SEQUENCE: 12

Phe Val Asn Gln His Leu Cys Gly Ser His Leu Val Glu Ala Leu Tyr
```

```
                1               5                   10                  15
Leu Val Cys Gly Glu Arg Gly Phe Phe Tyr Thr Asp Lys Thr Arg Gly
                        20                  25                  30

Ile Val Glu Gln Cys Cys Thr Ser Ile Cys Ser Leu Tyr Gln Leu Glu
            35                  40                  45

Asn Tyr Cys Asn
        50

<210> SEQ ID NO 13
<211> LENGTH: 52
<212> TYPE: PRT
<213> ORGANISM: Artificial sequence
<220> FEATURE:
<223> OTHER INFORMATION: Synthesized

<400> SEQUENCE: 13

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr Lys Gly
                        20                  25                  30

Ile Val Glu Gln Cys Cys Thr Ser Ile Cys Ser Leu Tyr Gln Leu Glu
            35                  40                  45

Asn Tyr Cys Asn
        50

<210> SEQ ID NO 14
<211> LENGTH: 116
<212> TYPE: PRT
<213> ORGANISM: Artificial sequence
<220> FEATURE:
<223> OTHER INFORMATION: Synthesized

<400> SEQUENCE: 14

Met Ala Thr His Ala Val Ser Val Leu Lys Gly Asp Gly Pro Val Gln
1               5                   10                  15

Gly Ile Ile Asn Phe Glu Gln His Glu Ser Asn Gly Pro Val Lys Val
                        20                  25                  30

Trp Gly Ser Ile His Gly Leu Thr Glu Gly Leu His Gly Phe His Val
            35                  40                  45

His Glu Phe Gly Asp Asn Thr Ala Gly Ser Thr Ser Ala Gly Pro Arg
        50                  55                  60

Phe Val Asn Gln His Leu Cys Gly Ser His Leu Val Glu Ala Leu Tyr
65                  70                  75                  80

Leu Val Cys Gly Glu Arg Gly Phe Phe Tyr Thr Asp Lys Thr Arg Gly
                        85                  90                  95

Ile Val Glu Gln Cys Cys Thr Ser Ile Cys Ser Leu Tyr Gln Leu Glu
                100                 105                 110

Asn Tyr Cys Asn
        115

<210> SEQ ID NO 15
<211> LENGTH: 116
<212> TYPE: PRT
<213> ORGANISM: Artificial sequence
<220> FEATURE:
<223> OTHER INFORMATION: Synthesized

<400> SEQUENCE: 15

Met Ala Thr His Ala Val Ser Val Leu Lys Gly Asp Gly Pro Val Gln
1               5                   10                  15
```

Gly Ile Ile Asn Phe Glu Gln His Glu Ser Asn Gly Pro Val Lys Val
                20                  25                  30

Trp Gly Ser Ile His Gly Leu Thr Glu Gly Leu His Gly Phe His Val
            35                  40                  45

His Glu Phe Gly Asp Asn Thr Ala Gly Ser Thr Ser Ala Gly Pro Lys
    50                  55                  60

Phe Val Asn Gln His Leu Cys Gly Ser His Leu Val Glu Ala Leu Tyr
65                  70                  75                  80

Leu Val Cys Gly Glu Arg Gly Phe Phe Tyr Thr Asp Lys Thr Lys Gly
                85                  90                  95

Ile Val Glu Gln Cys Cys Thr Ser Ile Cys Ser Leu Tyr Gln Leu Glu
                100                 105                 110

Asn Tyr Cys Asn
            115

<210> SEQ ID NO 16
<211> LENGTH: 116
<212> TYPE: PRT
<213> ORGANISM: Artificial sequence
<220> FEATURE:
<223> OTHER INFORMATION: Synthesized

<400> SEQUENCE: 16

Met Ala Thr Lys Ala Val Ser Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Ser Thr Ser Ala Gly Pro Arg
    50                  55                  60

Phe Val Asn Gln His Leu Cys Gly Ser His Leu Val Glu Ala Leu Tyr
65                  70                  75                  80

Leu Val Cys Gly Glu Arg Gly Phe Phe Tyr Thr Asp Lys Thr Arg Gly
                85                  90                  95

Ile Val Glu Gln Cys Cys Thr Ser Ile Cys Ser Leu Tyr Gln Leu Glu
                100                 105                 110

Asn Tyr Cys Asn
            115

<210> SEQ ID NO 17
<211> LENGTH: 116
<212> TYPE: PRT
<213> ORGANISM: Artificial sequence
<220> FEATURE:
<223> OTHER INFORMATION: Synthesized

<400> SEQUENCE: 17

Met Ala Thr Lys Ala Val Ser Val Leu Lys Gly Asp Gly Pro Val Gln
1               5                   10                  15

Gly Ile Ile Asn Phe Glu Gln Lys Glu Ser Asn Gly Pro Val Lys Val
                20                  25                  30

Trp Gly Ser Ile Lys Gly Leu Thr Glu Gly Leu His Gly Phe His Val
            35                  40                  45

His Glu Phe Gly Asp Asn Thr Ala Gly Ser Thr Ser Ala Gly Pro Lys
    50                  55                  60

Phe Val Asn Gln His Leu Cys Gly Ser His Leu Val Glu Ala Leu Tyr

```
                65                  70                  75                  80
        Leu Val Cys Gly Glu Arg Gly Phe Phe Tyr Thr Asp Lys Thr Lys Gly
                        85                  90                  95
        Ile Val Glu Gln Cys Cys Thr Ser Ile Cys Ser Leu Tyr Gln Leu Glu
                        100                 105                 110

Asn Tyr Cys Asn
                    115

<210> SEQ ID NO 18
<211> LENGTH: 351
<212> TYPE: DNA
<213> ORGANISM: Artificial sequence
<220> FEATURE:
<223> OTHER INFORMATION: Synthesized

<400> SEQUENCE: 18
atggcgacgc atgccgtgag cgtgctgaag ggcgacggcc cagtgcaggg catcatcaat       60
ttcgagcagc atgaaagtaa tggaccagtg aaggtgtggg aagcattca tggactgact       120 gaaggcctgc atggattcca tgttcatgag tttggagata atacagctgg ctctaccagt      180
gcaggtccgc ggtttgtgaa ccagcatctg tgcggcagcc atctggtgga agcgctgtat      240
ctggtgtgcg gcgaacgcgg cttctttat accgataaaa cccgcggcat tgtggaacag       300
tgctgcacca gcatttgcag cctgtatcag ctggaaaact attgcaacta a               351

<210> SEQ ID NO 19
<211> LENGTH: 351
<212> TYPE: DNA
<213> ORGANISM: Artificial sequence
<220> FEATURE:
<223> OTHER INFORMATION: Synthesized

<400> SEQUENCE: 19
atggcgacgc atgccgtgag cgtgctgaag ggcgacggcc cagtgcaggg catcatcaat       60
ttcgagcagc atgaaagtaa tggaccagtg aaggtgtggg aagcattca tggactgact       120 gaaggcctgc atggattcca tgttcatgag tttggagata atacagctgg ctctaccagt      180
gcaggtccga atttgtgaa ccagcatctg tgcggcagcc atctggtgga agcgctgtat       240
ctggtgtgcg gcgaacgcgg cttctttat accgataaaa cccgcggcat tgtggaacag       300
tgctgcacca gcatttgcag cctgtatcag ctggaaaact attgcaacta a               351

<210> SEQ ID NO 20
<211> LENGTH: 351
<212> TYPE: DNA
<213> ORGANISM: Artificial sequence
<220> FEATURE:
<223> OTHER INFORMATION: Synthesized

<400> SEQUENCE: 20
atggcgacga agccgtgag cgtgctgaag ggcgacggcc cagtgcaggg catcatcaat        60
ttcgagcaga agaaaagtaa tggaccagtg aaggtgtggg aagcattaa aggactgact       120 gaaggcctgc atggattcca tgttcatgag tttggagata atacagctgg ctctaccagt      180
gcaggtccgc ggtttgtgaa tcagcatctg tgcggcagcc atctggtgga agcgctgtat      240
ctggtgtgcg gcgaacgcgg cttctttat accgataaaa cccgcggcat tgtggaacag       300
tgctgcacca gcatttgcag cctgtatcag ctggaaaatt attgcaacta a               351

<210> SEQ ID NO 21
```

```
<211> LENGTH: 351
<212> TYPE: DNA
<213> ORGANISM: Artificial sequence
<220> FEATURE:
<223> OTHER INFORMATION: Synthesized

<400> SEQUENCE: 21
atggcgacga  aagccgtgag  cgtgctgaag  ggcgacggcc  cagtgcaggg  catcatcaat       60
ttcgagcaga  aagaaagtaa  tggaccagtg  aaggtgtggg  gaagcattaa  aggactgact      120
gaaggcctgc  atggattcca  tgttcatgag  tttggagata  atacagctgg  ctctaccagt      180
gcaggtccga  aatttgtgaa  tcagcatctg  tgcggcagcc  atctggtgga  agcgctgtat      240
ctggtgtgcg  gcgaacgcgg  cttcttttat  accgataaaa  cccgcggcat  tgtggaacag      300
tgctgcacca  gcatttgcag  cctgtatcag  ctggaaaatt  attgcaacta  a               351
```